(12) United States Patent
Burns et al.

(10) Patent No.: US 9,744,327 B1
(45) Date of Patent: Aug. 29, 2017

(54) FACIAL SKIN INDENTATION PREVENTER

(71) Applicants: Kathleen Burns, Pueblo, CO (US); Frances Burns, Pueblo, CO (US)

(72) Inventors: Kathleen Burns, Pueblo, CO (US); Frances Burns, Pueblo, CO (US)

( * ) Notice: Subject to any disclaimer, the term of this patent is extended or adjusted under 35 U.S.C. 154(b) by 0 days.

(21) Appl. No.: 15/052,397

(22) Filed: Feb. 24, 2016

(51) Int. Cl.
| | |
|---|---|
| *A61F 11/00* | (2006.01) |
| *A61M 15/08* | (2006.01) |
| *A62B 7/00* | (2006.01) |
| *A61M 16/06* | (2006.01) |
| *A41D 13/11* | (2006.01) |
| *A61M 25/02* | (2006.01) |

(52) U.S. Cl.
CPC ......... *A61M 16/0672* (2014.02); *A41D 13/11* (2013.01); *A61M 2025/0226* (2013.01); *A61M 2025/0266* (2013.01); *A61M 2209/06* (2013.01)

(58) Field of Classification Search
CPC .......... A61M 16/0672; A61M 16/0666; A61M 16/0683; A61M 2025/0266
USPC ............................................ 128/857, 207.18
See application file for complete search history.

(56) References Cited

U.S. PATENT DOCUMENTS

| | | | | | |
|---|---|---|---|---|---|
| 2,669,231 | A | * | 2/1954 | Bernard Fisher | A61M 25/02 |
| | | | | | 128/DIG. 26 |
| 3,630,195 | A | * | 12/1971 | Santomieri | A61M 25/02 |
| | | | | | 128/DIG. 26 |
| 3,834,380 | A | * | 9/1974 | Boyd | A61M 25/02 |
| | | | | | 128/DIG. 26 |
| 4,122,857 | A | * | 10/1978 | Haerr | A61M 25/02 |
| | | | | | 128/DIG. 26 |
| 4,333,468 | A | * | 6/1982 | Geist | A61M 25/02 |
| | | | | | 128/DIG. 26 |
| 4,336,806 | A | * | 6/1982 | Eldridge, Jr. | A61M 25/02 |
| | | | | | 128/DIG. 26 |
| 4,569,348 | A | * | 2/1986 | Hasslinger | A61M 25/02 |
| | | | | | 128/DIG. 15 |
| 4,699,139 | A | * | 10/1987 | Marshall | A61M 16/0666 |
| | | | | | 128/207.18 |
| 5,383,451 | A | * | 1/1995 | Delulio | A61M 16/0488 |
| | | | | | 128/207.17 |
| 5,509,409 | A | * | 4/1996 | Weatherholt | A61M 16/0666 |
| | | | | | 128/200.26 |
| 6,026,811 | A | * | 2/2000 | Settle | A61M 16/0666 |
| | | | | | 128/207.17 |
| 8,317,755 | B2 | * | 11/2012 | Morrison | A61M 25/02 |
| | | | | | 604/180 |
| 9,248,259 | B2 | * | 2/2016 | Kyvik | A61M 25/02 |
| 9,358,366 | B2 | * | 6/2016 | Kyvik | A61M 25/02 |
| 2013/0312760 | A1 | * | 11/2013 | Kostyk | A61M 16/0683 |
| | | | | | 128/207.18 |

\* cited by examiner

*Primary Examiner* — Kristen Matter

(57) ABSTRACT

A facial skin indentation preventer has a central base core surrounded by an entrapment flap and a securing flap. The core and flaps have two layers: a soft moleskin or similar skin-contact layer and a second more rigid layer. A rigid cushion is attached to the central base core and a cannula or similar item can be placed thereon. The flaps are then folded inwards, over the rigid cushion, creating a cannula pocket above the rigid cushion and entrapping and holding the cannula therein. An entrapment hinge and securing hinge ensure the folds remain rounded and soft. A flap attachment is used to lock the securing flap in place and ensure the cannula stays within the cannula pocket.

4 Claims, 4 Drawing Sheets

FACIAL SKIN INDENTATION PREVENTER

TECHNICAL FIELD

The present invention relates generally to the fields of health and beauty, and more particularly to a facial skin indentation preventer.

BACKGROUND

Human skin, especially facial skin, can be sensitive. Items that rub, press into, or otherwise contact skin for extended periods can lead to redness, indentation, irritation, swelling, and even sores. This is especially true for items such as mask straps, cannulas, and similar objects (collectively, "cannulas") that put constant pressure on the facial skin over longer periods of time. For example, many people utilize nasal cannulas for delivery of supplemental oxygen. The hollow plastic tubing that feeds the oxygen usually runs from behind the ears to the nose. If worn during sleep, such tubing is often pressed into the wearer's facial skin causing red, irritated indentations or "lines" across the wearer's cheeks. Such lines can persist for hours after removal of the causative agent (i.e., the cannula, mask strap, etc.) and can be unsightly as well as unhealthy.

Therefore, what is needed is a device that can be used in combination with cannulas that works to prevent facial skin indentations, irritations, etc.

DETAILED DESCRIPTION

Figure 1:
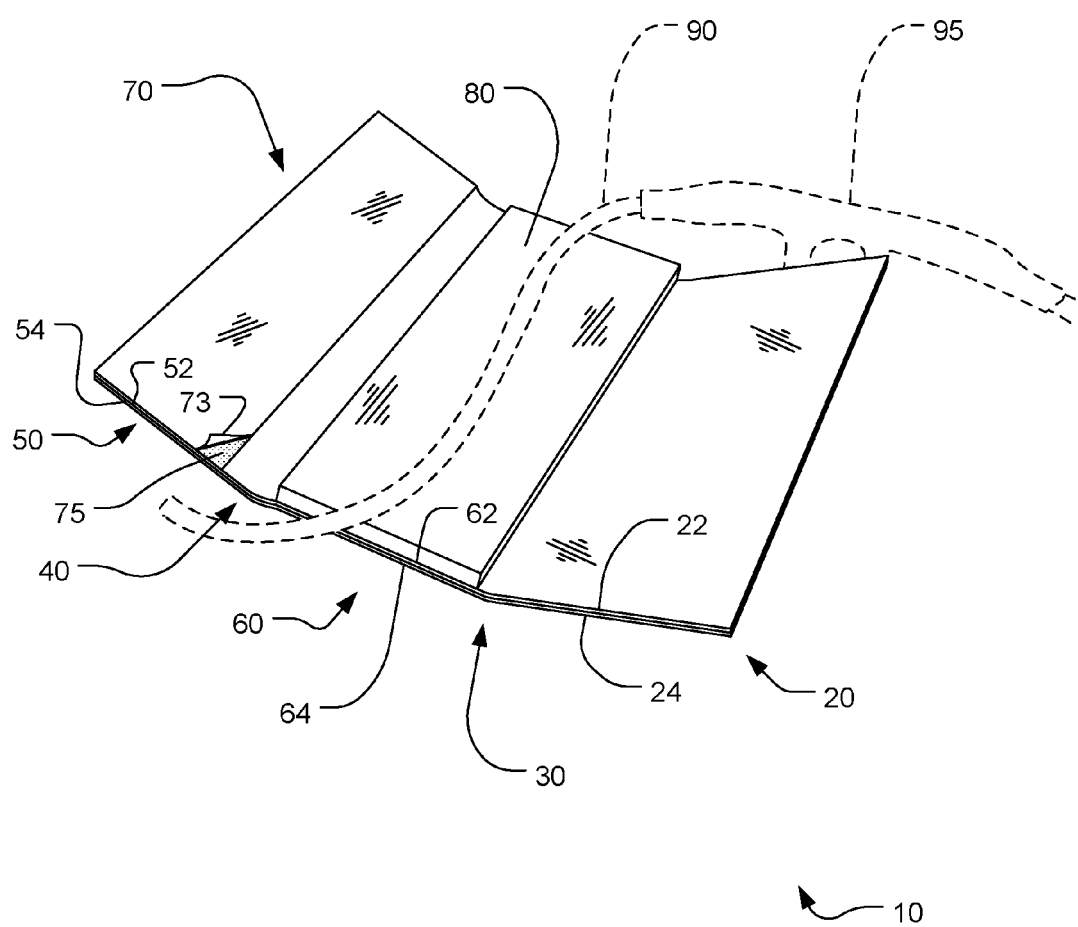
FIG. 1 illustrates a perspective view of an exemplary embodiment of a facial skin indentation preventer in a pre-installation configuration.

In the following discussion, numerous specific details are set forth to provide a thorough understanding of the present disclosure. However, those skilled in the art will appreciate that embodiments may be practiced without such specific details. Furthermore, lists and/or examples are often provided and should be interpreted as exemplary only and in no way limiting embodiments to only those examples.

Exemplary embodiments are described below in the accompanying Figure. The following detailed description provides a comprehensive review of the drawing in order to provide a thorough understanding of, and an enabling description for, these embodiments. One having ordinary skill in the art will understand that in some cases well-known structures and functions have not been shown or described in detail to avoid unnecessarily obscuring the description of the embodiments.

Referring now to the drawings, FIG. 1 illustrates a perspective view of an exemplary embodiment of a facial skin indentation preventer 10 in a pre-installation configuration. The preventer 10 is shown in an open configuration with a cannula tube 90 attached to nasal prongs 95 (both shown in broken lines) placed on top of the preventer 10. The embodiment of the preventer 10 illustrated in FIG. 1 comprises a central base core 60, an entrapment flap 20, a securing flap 50, an entrapment hinge 30, a securing hinge 40, and a flap attachment 70. It is important to understand that the preventer 10 can be utilized with any strap, tube, or similar object (again, collectively "cannulas") that would otherwise press into the skin of a user.

The central base core 60, the entrapment flap 20, and the securing flap 50 are illustrated in FIG. 1 as each comprising a plurality of layers. The plurality of layers includes an outer skin-contact layer 24, 64 and 54 and an inner rigidity layer 22, 62 and 52. The outer skin-contact layer 24, 64 and 54 can comprise a soft, resilient material such as mole-skin or other similarly soft fabric or material. The inner rigidity layer 22, 62 and 52 should be a somewhat stiff/rigid material that is still flexible, but has enough stiffness so that the preventer 10 does not completely mold to the curvature of the face when the cannula 90 that is running through the preventer 10 is pulled tight against the face, or that the edges of the preventer 10 will at least spring back up off the face when the strain on a cannula 90 is relaxed. A stiff non-stick and/or waxed paper can be used for the inner rigidity layer 22, 62 and 52, while other materials are contemplated in other embodiments.

The central base core 60 can be generally rectangular in shape, 1.5 inches wide by 3.5 inches long. In other embodiments, other widths and lengths are contemplated. Attached to the central base core 60 on one long side is an entrapment flap 20. Attached on the other long side is a securing flap 50.

In order to install the preventer 10 on the cannula tubing 90, the user simply places the cannula tubing 90 lengthwise along the center of the central base core 60 and the traps the tubing 90 in place by folding the entrapment flap 20 over the tube, thereby sandwiching the cannula 90 between the entrapment flap 20 and the central base core 60. In order to ensure the cannula stays in place, the user then folds the securing flap 50 over top of the entrapment flap 20 and locks it in place. In the embodiment illustrated in FIG. 1, a flap attachment 70 is used to lock the securing flap 50 in place. This is accomplished by removing the adhesive cover 73 from the securing flap adhesive 75 in order to expose the adhesive before folding the securing flap 50 over. Then, the user simply presses the adhesive onto the entrapment flap 20 and locks the two together. The cannula is thereby trapped between the entrapment flap 20 and the central base core 60 and secured therein by attachment of the securing flap 50 to the entrapment flap 70. In other embodiments, other means of entrapping the cannula on top of the central base core 60 are contemplated. For example, one or more small spring clamps could grasp the cannula tubing, or a sandwich of hook and loop material with the tubing therebetween could be used, etc. However, embodiment illustrated in FIG. 1 provides a number of advantages over these other embodiments: it is simple to manufacture; provides smooth, rounded side edges; provides a soft skin-contact surface whether the preventer 10 is upside-down or right-side-up; etc.

Figure 4:
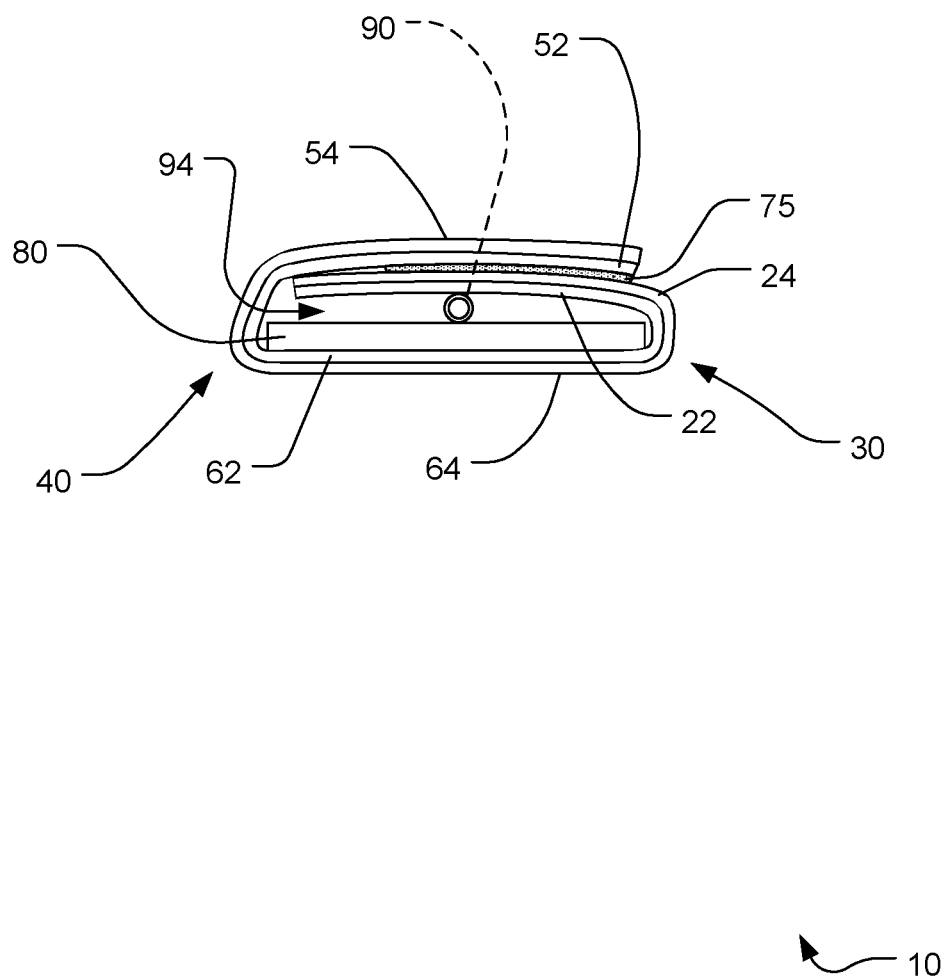
FIG. 4 illustrates a side elevation view of an exemplary embodiment of a facial skin indentation preventer in an installed position around a cannula tube.

Between the entrapment flap 20 and the central base core 60 is an area called an entrapment hinge 30 that provides extra materials that can act as a hinge when the entrapment flap 20 is folded back over the central base core 60 during installation (see FIG. 4). Similarly, between the securing flap 50 and the central base core 60 is an area called a securing hinge 40 that provides extra materials that can act as a hinge when the securing flap 50 is folded back over the central base core 60 during installation (see FIG. 4). When the two flaps 20 and 50 are folded over during installation, the two hinges 30 and 40 form soft, rounded edges that run the length of the long sides of the central base core 60. These soft, rounded edges are much preferable to sharp, distinct edges that would otherwise be found if the flaps weren't folded over but were instead separate pieces stacked on top of the central base core 60 (or in the case of only one of the two flaps being used).

The central base core 60 has attached thereto a rigid cushion 80 comprising a double-sided foam tape or any other suitably stiff and cushiony material. A one-thirty-second inch or one-sixteenth inch thickness can be used. Other thicknesses can be used in other embodiments. Double-sided foam tape allows the material to be easily attached to the inner rigidity layer 62 of the central base core (by simply peeling off the adhesive protection from the bottom of the foam tape and sticking it to the top of the central base core 62). The top surface of the second tape can be left with the adhesive cover in place to ensure that the cannula can be slid back and forth over the rigid cushion 80 in order to reposition the preventer 10 along the length of the cannula 90 as desired. Alternatively, the second tape can have the adhesive cover removed and the preventer 10 can then be attached to the cannula 90 at a specific location. In yet other embodiments, other somewhat rigid cushiony material(s) can be used instead of double-sided foam tape. The rigid cushion 80 may have adhesives on zero, one, two or more faces and may attach to the inner rigidity layer 62 in other ways.

In yet another embodiment, the flap attachment 70 can be pre-installed on the outer skin-contact layer 24 of the entrapment flap 20. In this configuration, once the entrapment flap 20 is closed over the cannula 90, then the adhesive cover 73 can be removed from the flap attachment 70 in order to expose the flap adhesive 75 and then the securing flap 50 can be folded over onto the adhesive, thereby locking the two flaps together.

Figure 2:
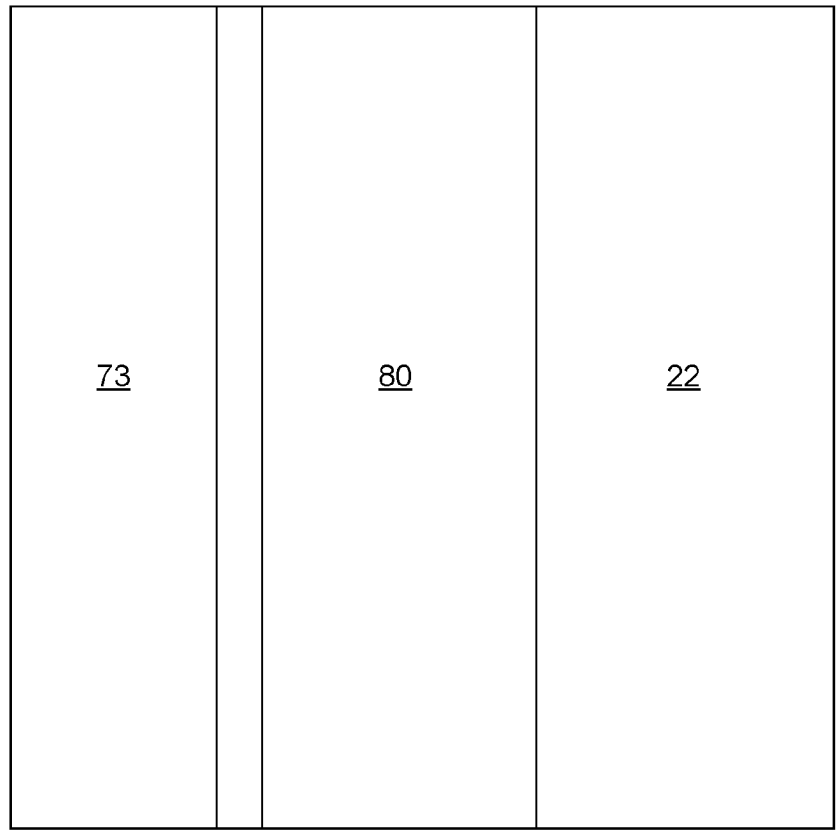
FIG. 2 illustrates a top plan view of an exemplary embodiment of a facial skin indentation preventer in a pre-installation configuration.

FIG. 2 illustrates a top plan view of an exemplary embodiment of a facial skin indentation preventer 10 in a pre-installation configuration. When viewed from above, only the top surfaces of the pre-installation preventer 10 are visible: the inner rigidity layer 22 of the entrapment flap 20, the rigid cushion 80 on top of the central base core 60, and the adhesive cover 73 of the flap attachment 70 on top of the securing flap 50. Also, the entrapment hinge 30 and securing hinge 40 areas are visible.

Figure 3:
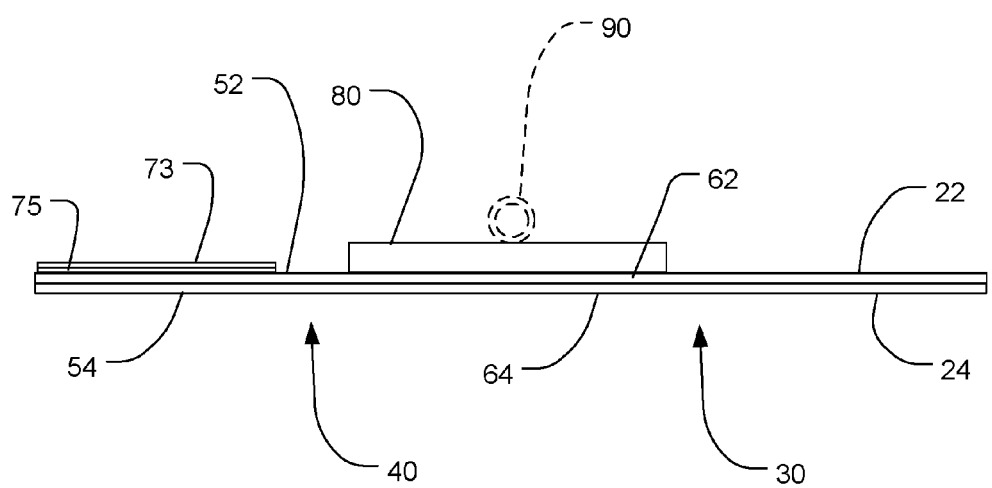
FIG. 3 illustrates a side elevation view of an exemplary embodiment of a facial skin indentation preventer in a pre-installation configuration.

FIG. 3 illustrates a side elevation view of an exemplary embodiment of a facial skin indentation preventer 10 in a pre-installation configuration. In the side view, the two layers that make up the entrapment flap 20, central base core 60, securing flap 50, and hinges 30 and 40 are visible: the outer skin-contact layer 24, 64 and 54 and the inner rigidity layer 22, 62 and 52. Similarly, the two layers that make up the flap attachment 70 are visible as well: the adhesive cover 73 and the securing flap adhesive 75. During installation, the adhesive cover 73 is removed, exposing the securing flap adhesive 75 for attachment to the outer skin-contact layer 24 of the entrapment flap 20.

Note the round cannula tube 90 is illustrated in FIG. 3 using broken lines. The cannula tube is placed atop and along approximately the center of the rigid cushion 80. The entrapment flap 20 can then be folded along the entrapment hinge 30 to trap the cannula between the entrapment flap 20 and the rigid cushion 80. The securing flap 50 can then be folded along the securing hinge 40 to secure the cannula in place. The flap attachment 70 ensures that the installed preventer 10 is able to keep the cannula in place during repositioning of the user, changing the location of the preventer 10 along the cannula tubing, etc.

FIG. 4 illustrates a side elevation view of an exemplary embodiment of a facial skin indentation preventer 10 in an installed position around a cannula tube 90. In its installed configuration, the preventer 10 creates a cannula pocket 94 which is a space within which a cannula 90 can rest. It is important to understand that the preventer 10 can be utilized with any strap, tube, or similar object (again, collectively "cannulas") that would otherwise press into the skin of a user. Thus, the cannula pocket 94 is designed to hold within it any strap, tube or similar object, not just a cannula. The cannula pocket 94 is created when the inner rigidity layer 22 of the entrapment flap 20 is brought near the top surface of the rigid cushion 80. This occurs when the entrapment flap 20 is folded along the entrapment hinge 30 and placed over the central base core 60.

In this illustration, the rounded long edges of the preventer 10 are apparent as the hinges 30 and 40 are illustrated in their hinged configuration rather than flat as in FIGS. 2 and 3. The cannula tubing 90 is clearly illustrated as being entrapped in the cannula pocket 94, i.e., the space between the inner rigidity layer 22 of the entrapment flap 20 and the top surface of the rigid cushion 80 of the central base core 60.

The overlapping of the dual-layer entrapment and securing flaps above the tubing 90 ensures proper cushioning should the preventer 10 get flipped over and present the outer skin-contact layer 54 of the securing flap 50 to the user's facial skin instead of the outer skin-contact layer 64 of the central base core 60, as is the norm. In either case, the user can roll-over onto the cannula tubing 90 when sleeping, and yet the preventer 10 will distribute the pressure from the tubing 90 across a wider surface area and ensure that the user doesn't awake with a red, irritated indentation from the cannula tubing pressing into their cheek or other skin.

It should be apparent from the above discussion that any other strap, tube, cord, or material can be wrapped with the preventer 10 and it will ensure the prevention of skin indentation therefrom. Similarly, the preventer 10 can be used on straps, tubes, cords, or other materials that contact other portions of a person's skin in addition to those touching the facial skin and will similarly prevent those materials from causing uncomfortable and unsightly indentations.

While particular embodiments have been described and disclosed in the present application, it is clear that any number of permutations, modifications, or embodiments may be made without departing from the spirit and the scope of this disclosure.

Particular terminology used when describing certain features or aspects of the embodiments should not be taken to imply that the terminology is being redefined herein to be restricted to any specific characteristics, features, or aspects with which that terminology is associated. In general, the terms used in the following claims should not be construed to be limited to the specific embodiments disclosed in the specification, unless the above Detailed Description section explicitly defines such terms. Accordingly, the actual scope of the claims encompasses not only the disclosed embodiments, but also all equivalent ways of practicing or implementing the claimed subject matter.

The above detailed description of the embodiments is not intended to be exhaustive or to limit the invention to the precise embodiment or form disclosed herein or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

Any patents, applications and other references that may be listed in accompanying or subsequent filing papers, are incorporated herein by reference. Aspects of the invention can be modified, if necessary, to employ the systems, functions, and concepts of the various references to provide yet further embodiments of the invention.

In light of the above "Detailed Description," the Inventor may make changes to the invention. While the detailed description outlines possible embodiments of the invention and discloses the best mode contemplated, no matter how detailed the above appears in text, the invention may be practiced in a myriad of ways. Thus, implementation details may vary considerably while still being encompassed by the spirit of the invention as disclosed by the inventors. As discussed herein, specific terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

The above specification, examples and data provide a description of the structure and use of exemplary implementations of the described articles of manufacture and methods. It is important to note that many implementations can be made without departing from the spirit and scope of the invention.

What is claimed is:

1. A facial skin indentation preventer, comprising:
an outer skin-contact layer for contacting a face of a wearer, the outer skin-contact layer comprising non-adhesive fabric;
an inner rigidity layer that is made from a stiffer material than the outer skin-contact layer;
a rigid cushion attached to the inner rigidity layer in a center of the preventer, the center of the preventer defining a central base core;
one end of the preventer defining an entrapment flap;
attached to the central base core by an entrapment hinge, the entrapment flap configured to be folded towards the rigid cushion so as to present a first rounded, soft edge;
a second end of the preventer defining a securing flap attached to the central base core by a securing hinge;
the securing flap configured to be folded towards the rigid cushion so as to present a second rounded, soft edge;
a flap attachment secured to the securing flap for securing the securing flap to the entrapment flap in a folded position defining a cannula pocket space configured for holding cannula tubing; and
wherein the preventer is configured for distributing pressure from the cannula tubing across a wider surface area to prevent indentations in the facial skin of the wearer during use of the cannula tubing.

2. The facial skin indentation preventer of claim 1, wherein the flap attachment comprises a flap adhesive and an adhesive cover attached thereto, whereby removal of the adhesive cover from the flap adhesive exposes the flap adhesive so that the entrapment flap can affix thereto.

3. The facial skin indentation preventer of claim 2, wherein the outer skin-contact layer is moleskin.

4. The facial skin indentation preventer of claim 1, wherein the outer skin-contact layer is moleskin.

* * * * *